United States Patent
Will, IV

(10) Patent No.: US 10,972,891 B2
(45) Date of Patent: Apr. 6, 2021

(54) AUTOMATED MEDICAL ITEM DELIVERY APPARATUS

(71) Applicant: INTERNATIONAL BUSINESS MACHINES CORPORATION, Armonk, NY (US)

(72) Inventor: Henry C. Will, IV, Dover, NJ (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 127 days.

(21) Appl. No.: 16/165,697

(22) Filed: Oct. 19, 2018

(65) Prior Publication Data

US 2020/0121533 A1 Apr. 23, 2020

(51) Int. Cl.
*H04W 4/90* (2018.01)
*H04W 4/021* (2018.01)
(Continued)

(52) U.S. Cl.
CPC ............. *H04W 4/90* (2018.02); *B64C 39/024* (2013.01); *G08B 21/18* (2013.01); *G08G 1/202* (2013.01); *G09B 23/28* (2013.01); *G16H 40/63* (2018.01); *A61G 2203/22* (2013.01); *B64C 2201/00* (2013.01); *G05D 1/0088* (2013.01); *G07C 2009/0092* (2013.01)

(58) Field of Classification Search
CPC ..................................................... G16H 40/20
See application file for complete search history.

(56) References Cited

U.S. PATENT DOCUMENTS 8,182,271 B2 * 5/2012 Socher ................. G09B 23/286
434/322
8,930,044 B1 1/2015 Peeters et al.
(Continued)

FOREIGN PATENT DOCUMENTS

KR 2017009251 A 7/2015

OTHER PUBLICATIONS

Boutilier, et al., "Optimizing a Drone Network to Deliver Automated External Defibrillators," Circulation. 2017; Circulationaha. 116.026318, originally published Mar. 2, 2017; pp. 1-51.
(Continued)

*Primary Examiner* — Thomas Randazzo
(74) *Attorney, Agent, or Firm* — Conley Rose, P.C.

(57) ABSTRACT

A computer-implemented method for automated delivery of a medical item. The method receives registration information for a plurality of trained users. The registration information includes a registration code indicating that a user is trained in a use of a medical item. The method tracks locations of the trained users via an end user device of the trained users. The method receives a medical alert indicating a medical emergency at a location. The method identifies a medical item that would assist in the medical emergency. The method identifies a trained user near the location corresponding to the medical emergency trained in use of the medical item. The method dispatches an autonomous delivery device to deliver the medical item to the location corresponding to the medical alert. The method alerts the trained user that the medical item is being dispatched to the location of the medical emergency.

20 Claims, 5 Drawing Sheets

(51) Int. Cl.
*B64C 39/02* (2006.01)
*G16H 40/20* (2018.01)
*G16H 40/63* (2018.01)
*G08B 21/18* (2006.01)
*G09B 23/28* (2006.01)
*G08G 1/00* (2006.01)
*G05D 1/00* (2006.01)
*G07C 9/00* (2020.01)

(56) References Cited

U.S. PATENT DOCUMENTS

| | | | |
|---|---|---|---|
| 8,948,935 B1 | 2/2015 | Peeters et al. | |
| 9,307,383 B1* | 4/2016 | Patrick | H04W 4/90 |
| 9,594,372 B1 | 3/2017 | Sills et al. | |
| 10,028,606 B1* | 7/2018 | Ritchie | G07C 9/00912 |
| 10,438,497 B2* | 10/2019 | Patrickson | G06Q 30/018 |
| 2009/0006258 A1* | 1/2009 | Ross | H04L 9/0838 |
| | | | 705/59 |
| 2011/0130636 A1 | 6/2011 | Daniel et al. | |
| 2014/0356834 A1* | 12/2014 | Patrickson | G06F 16/23 |
| | | | 434/262 |
| 2015/0148988 A1* | 5/2015 | Fleck | B64D 1/14 |
| | | | 701/2 |
| 2016/0125765 A1* | 5/2016 | Meretei | G09B 5/02 |
| | | | 434/262 |
| 2017/0115125 A1* | 4/2017 | Outwater | H04W 4/40 |
| 2017/0137124 A1* | 5/2017 | Walker | G08B 25/10 |
| 2017/0330436 A1* | 11/2017 | Williams | G08B 21/0236 |
| 2017/0341611 A1* | 11/2017 | Baker | B60R 25/305 |
| 2017/0369167 A1 | 12/2017 | Meadow | |
| 2018/0174102 A1* | 6/2018 | Winkle | G06Q 10/08355 |
| 2018/0242125 A1* | 8/2018 | Klein | H04W 4/90 |
| 2018/0242375 A1* | 8/2018 | O'Herlihy | H04W 4/40 |
| 2019/0387386 A1* | 12/2019 | Sethi | H04B 7/0413 |
| 2020/0050978 A1* | 2/2020 | Perez Barrera | G06Q 50/30 |
| 2020/0229267 A1* | 7/2020 | Arngren | H04W 8/005 |

OTHER PUBLICATIONS

Fleck, et al. "Usability of Lightweight Defibrillators for UAV Delivery." In Proceedings of the 2016 CHI Conference Extended Abstracts on Human Factors in Computing Systems (CHI EA '16). ACM, New York, NY, USA, 2016, pp. 3056-3061.

Kristensen, "Unmanned Aerial System for Fast Response to Medical Emergencies due to Traffic Accidents." World Academy of Science, Engineering and Technology International Journal of Health and Medical Engineering. vol. 11, No. 11, 2017, pp. 1-5.

Dayananda, et al., "An interconnected architecture for an emergency medical response unmanned aerial system," 2017 IEEE/AIAA 36th Digital Avionics Systems Conference (DASC), St. Petersburg, FL. 2017, pp. 1-6.

Dhivya, et al., "Quadcopter based technology for an emergency healthcare," 2017 Third International Conference on Biosignals, Images and Instrumentation (ICBSII), Chennai, 2017, pp. 1-3.

Bravo, et al., "First aid drone for outdoor sports activities," 2016 1st International Conference on Technology and Innovation in Sports, Health and Wellbeing (TISHW), Vila Real, 2016, pp. 1-5.

* cited by examiner

US 10,972,891 B2

AUTOMATED MEDICAL ITEM DELIVERY APPARATUS

BACKGROUND

In an emergency situation, it is critical that medical aid be administered at the earliest possible time. Not having the proper medical equipment, item, or train personnel can delay administering assistance during this critical time. Accordingly, the present disclosure describes several embodiments that allow for automated delivery of a medical item to a location where such medical assistance is needed.

SUMMARY

The present disclosure provides various embodiments of system, computer program product, and computer-implemented method for automated delivery of a medical item using an autonomous delivery device. As an example embodiment, the method receives registration information for a plurality of trained users. The registration information includes a registration code indicating that a user is trained in a use of a medical item. The method tracks locations of the trained users via an end user device of the trained users. The method receives a medical alert indicating a medical emergency at a location. The method identifies a medical item that would assist in the medical emergency. The method identifies a trained user near the location corresponding to the medical emergency trained in use of the medical item. The method dispatches an autonomous delivery device to deliver the medical item to the location corresponding to the medical alert. The method alerts the trained user that the medical item is being dispatched to the location of the medical emergency.

Other embodiments and advantages of the disclosed embodiments are further described in the detailed description.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

The illustrated figures are only exemplary and are not intended to assert or imply any limitation with regard to the environment, architecture, design, or process in which different embodiments may be implemented.

DETAILED DESCRIPTION

It should be understood at the outset that, although an illustrative implementation of one or more embodiments are provided below, the disclosed systems, computer program product, and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

As used within the written disclosure and in the claims, the terms "including" and "comprising" are used in an open-ended fashion, and thus should be interpreted to mean "including, but not limited to". Unless otherwise indicated, as used throughout this document, "or" does not require mutual exclusivity, and the singular forms "a", "an" and "the" are intended to include the plural forms as well, unless the context clearly indicates otherwise.

A module or unit as referenced herein can comprise one or more hardware or electrical components such as electrical circuitry, processors, and memory that may be specially configured to perform a particular function. The memory may be volatile memory or non-volatile memory that stores data such as, but not limited to, computer executable instructions, machine code, and other various forms of data. The module or unit may be configured to use the data to execute one or more instructions to perform one or more tasks. In certain instances, a module may also refer to a particular set of functions, software instructions, or circuitry that is configured to perform a specific task. For example, a module may comprise of software components such as, but not limited to, data access objects, service components, user interface components, application programming interface (API) components; hardware components such as electrical circuitry, processors, and memory; and/or a combination thereof. As referenced herein, computer executable instructions may be in any form including, but not limited to, machine code, assembly code, and high-level programming code written in any programming language.

Figure 1:
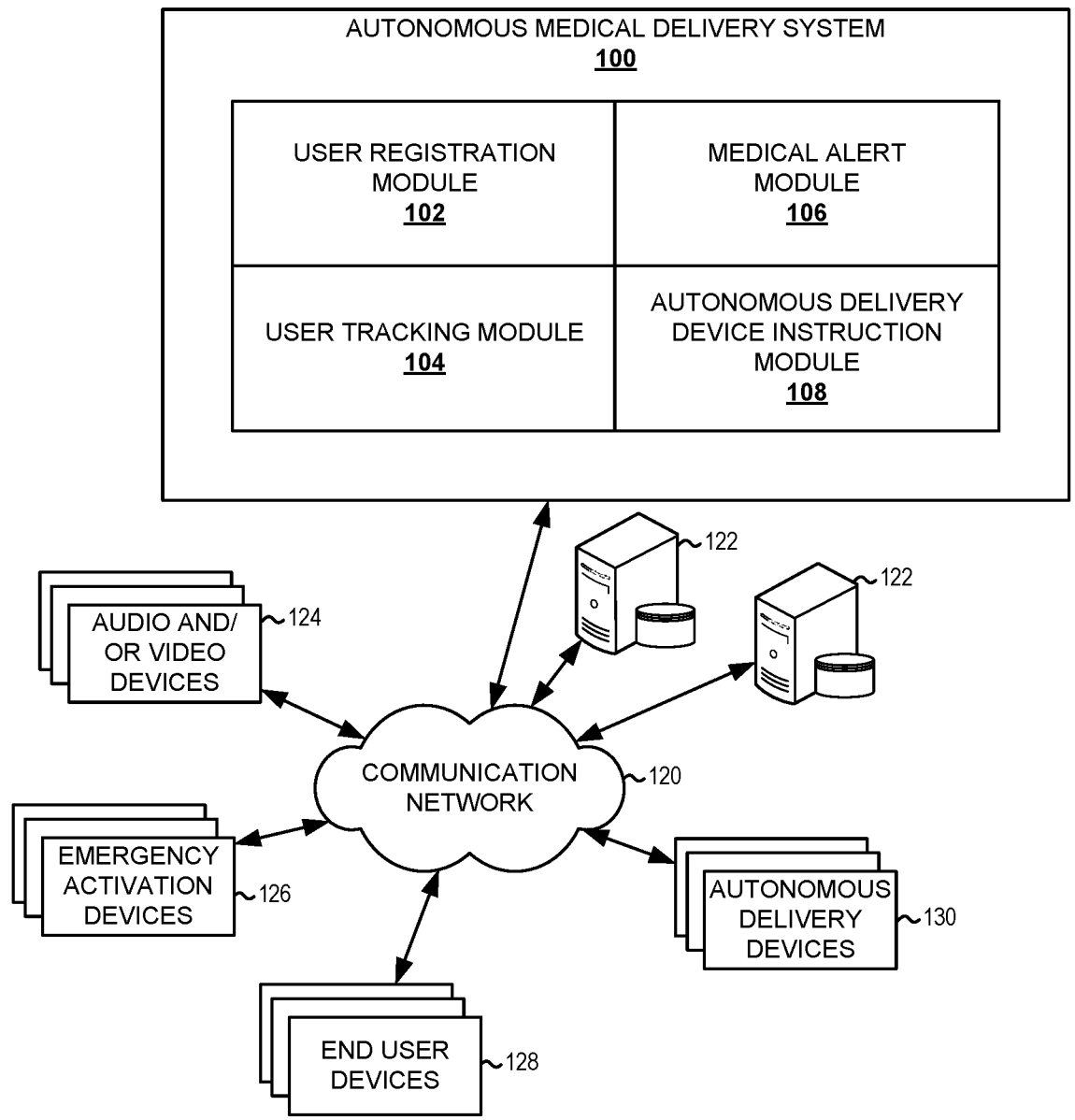
FIG. 1 is a schematic diagram illustrating an autonomous medical delivery system in accordance with an embodiment of the present disclosure.

FIG. 1 is a schematic diagram illustrating an autonomous medical delivery system 100 in accordance with an embodiment of the present disclosure. The autonomous medical delivery system 100 is configured to communicate with a plurality of devices over a communication network 120 including, but not limited to, one or more network devices 122, audio and/or video devices 124, emergency activation devices 126, end user devices 128, and autonomous delivery devices 130 to enable automated delivery of a medical item. In embodiments, the medical item can be any type of medical device, supplies, or medication. For example, the medical item can be an automated external defibrillator (AED), which is a portable device that can be used to resuscitate patients after cardiopulmonary resuscitation (CPR), has proven ineffective. An AED can check the heart rhythm and can send an electric shock to the heart to try to restore a normal rhythm. It is also envisioned that in certain embodiments the autonomous medical delivery system 100 can be used to deliver any type of item, not necessarily medical in nature. Further, in some embodiments, the autonomous medical delivery system 100 can be used to delivery instructions instead of or in addition to a medical item. For example, instructions on first aid, the Heimlich maneuver, or CPR.

As used herein, the term "communicate(s)" means capable of sending and/or receiving data over a communication link. The communication link can include both wired and wireless links, and may be a direct link or may comprise of multiple links passing through one or more communication networks or network devices such as, but not limited to, routers, firewalls, servers, and switches. In certain embodiments, the term communicates can also encompass internal communication between various components of a system and/or with an external input/output device such as a keyboard or display device.

The communication network 120 can include any type of wired or wireless network such as, but not limited to, local-area networks (LANs), wide-area networks (WANs), metropolitan-area networks (MANs), and one or more mobile networks. The communication network 120 can also include private networks and/or public networks such as the Internet.

The network devices 122 can be any type of server, database, knowledge base, or other types of data repository or service device that the autonomous medical delivery system 100 may communicate with in order to provide automated delivery of a medical item. For example, in certain embodiments, the network devices 122 can provide services or other data such as, but not limited to, maps, medical instructions, medical contacts, and emergency notification services.

The audio and/or video devices 124 can be any type of electronic device capable of capturing audio and/or video. For example, the audio and/or video devices 124 can be one or more audio sensors, microphones, video cameras, or other similar devices. The emergency activation devices 126 are devices (e.g., a push button or an emergency lever) that are set up at predetermined locations for enabling a user to trigger an alert. For example, the emergency activation devices 126 can be located at various locations on a school campus, within a building, a public park, an amusement park, an airport, a ski resort, or any other location. The audio and/or video devices 124 and the emergency activation devices 126 can be devices that are set up to exclusively communicate with the autonomous medical delivery system 100 or can be part of another system such as security monitoring system.

The end user devices 128 can be any type of personal electronic device such as, but not limited to, a smart phone, tablet, personal computer, smart watch, and kiosk or some other medical entry terminal that is capable of communicating with the autonomous medical delivery system 100. In certain embodiments, the end user devices 128 may include a specially configured application for communicating with the autonomous medical delivery system 100. For example, in certain embodiments, the end user devices 128 can be used to alert the autonomous medical delivery system 100 of a medical emergency and request a particular medical item. In some embodiments, the end user devices 128 can also be used to receive prerecorded medical instructions for using a medical item and/or can be used to receive live instructions from medical personnel.

The autonomous delivery devices 130 can be any type of unmanned automated delivery device or machine such as, but not limited to, a drone, a robot, and an autonomous vehicle. As non-limiting examples, there are current automated robots that provide security patrol or drones that deliver packages that can be configured to deliver a medical item in accordance with the present disclosure. In various embodiments, the autonomous delivery devices 130 can include a visual display, video/audio components, and network communication components for enabling a prerecorded instructional video or live communication to assist a user in an emergency situation. In some embodiments, the autonomous delivery devices 130 can also include a secure compartment or other security components for securing a medical item. In one embodiment, the medical item is only accessible if a security/unlock code is successfully entered.

In the depicted embodiment, the autonomous medical delivery system 100 includes a user registration module 102, a user tracking module 104, a medical alert module 106, and an autonomous delivery device instruction module 108 to enable automated delivery of a medical item using the autonomous delivery devices 130.

In one embodiment, the user registration module 102 is configured to register certified or trained users of a medical item. For example, in one embodiment, after a person has completed CPR training (or training in the use of an AED or other medical item), the person is provided with a registration code. The registration code can be provided physically to the person (e.g., on a certificate of completion), via email, text, or through some other form of electronic communication. Using an end user device 128, the trained person can download an application or visit a website associated with the autonomous medical delivery system 100 to register as a trained user of the medical item using the registration code. As part of the registration process, the user can provide supplementary information such as any additional medical training, education, or employment history, and user biometrics, voice sample, or facial image for security access purposes as further described below. The user can register a particular end user device 128 and grant permission for location tracking of the end user device 128 (e.g., using the global positioning system (GPS) component in the end user device 128) to enable medical emergency alerts. The autonomous medical delivery system 100 verifies the user information and registration code, and confirms or denies the user registration.

The user tracking module 104 is configured to keep track of the location of the various registered users based on the location of their end user device 128. In one embodiment, the user tracking module 104 may maintain a data table that stores the location of a medical item and the end user devices 128 that are located within a predetermined vicinity of the medical item (or the closest end user devices 128 to a medical item).

The medical alert module 106 is configured to monitor for medical alerts. The medical alerts can be received from various sources including, but not limited to, audio and/or video devices 124, emergency activation devices 126, end user devices 128, or other medical emergency services. For example, a user registered with the autonomous medical delivery system 100, using an end user device 128, can transmit an alert to the autonomous medical delivery system 100 using an application, text, website, or via other electronic communications to the autonomous medical delivery system 100 to alert the autonomous medical delivery system 100 of a medical emergency. In some embodiments, the medical alert may include information regarding the type of emergency (e.g., suspected heart attack, seizure, gunshot wound, etc.), number of patients (e.g., mass casualties), requested medical items, request for security/police assistance, and any other related information. In some embodiments, the medical alert module 106 can be configured to receive medical alerts from emergency services providers such as 911 services because medical items and trained personnel may be able to assist a person in distress prior to 911 services arriving at a location.

In one embodiment, the medical alert module 106 is configured to analyze audio and/or video received from the audio and/or video devices 124 to determine if there is a medical alert. For example, the medical alert module 106 can analyze audio to identify calls for help (e.g., someone screaming "help" or "call 911"). In some embodiments, the medical alert module 106 is configured to determine an approximate location associated with the verbal alert based on analyzing the audio signals received from multiple audio and/or video devices 124. For example, in one embodiment, based on the intensity of the audio signals associated with the help request and the locations of the receiving audio and/or video devices 124, the medical alert module 106 can determine an approximate location associated with the verbal alert. In some embodiments, the medical alert module 106 can also be configured to analyze video to identify movements, positions, or actions associated with a person in distress or other objects such as, but not limited to, a person falling or laying on the ground, movements associated with a seizure or a heart attack, a person administering CPR, a vehicle accident, and a train or plane crash. In an embodiment, the medical alert module 106 can also be configured to analyze audio/video to validate that an emergency actually exists to rule out false positives. For example, in an embodiment, the medical alert module 106 could use audio/video/sensory means to identify a car accident, tornado destruction, etc.

The autonomous delivery device instruction module 108 is configured to select one or more autonomous delivery devices 130 (e.g., based on their size, medical item to be deliver, location) and transmit instructions to the selected one or more autonomous delivery devices 130 to deliver one or more medical items to a location associated with a medical alert. In some embodiments, in response to identifying a medical emergency or receiving a medical alert, the autonomous delivery device instruction module 108 can instruct one or more autonomous delivery devices 130 to deliver one or more medical items to an area nearby the medical emergency so that the medical item is closer to the medical emergency to increase efficiency in delivering the medical item to the medical emergency location if needed. The instructions can include the type/number of medical items, the location of the medical emergency, and security/access information for unlocking or releasing the medical item from the autonomous delivery devices 130. For example, in one embodiment, an access code can be sent to an end user device 128 of a trained user responding to the medical alert that enables the unlocking or release of a medical item from an autonomous delivery device 130. In some embodiments, an access code may also be provided the autonomous delivery devices 130 to enable the autonomous delivery devices 130 to access a medical item from a secure storage container/area. Alternative security measurements can also be implemented including, but are not limited to, utilizing the previous registration code as a security code, a verbal passcode, facial recognition, voice recognition, or biometric recognition such as a thumbprint. In some embodiments, if the medical items are not needed for the medical emergency, the autonomous delivery device instruction module 108 can instruct one or more autonomous delivery devices 130 to return the one or more medical items to their prior locations. The autonomous delivery device instruction module 108 can also be configured to provide instructional audio or video for using the medical item. Alternatively, the autonomous delivery device instruction module 108 can be configured to provide a live communication feed with medical personnel to assist a user with administrating medical aid using the medical item. Further, in some embodiments, the autonomous delivery device instruction module 108 can be configured to deliver a medical item to a particular location at a particular time. For example, a registered user (e.g. a doctor or pharmacist) could request to have a drug or device delivered to a particular location at a predetermined time.

Figure 2:
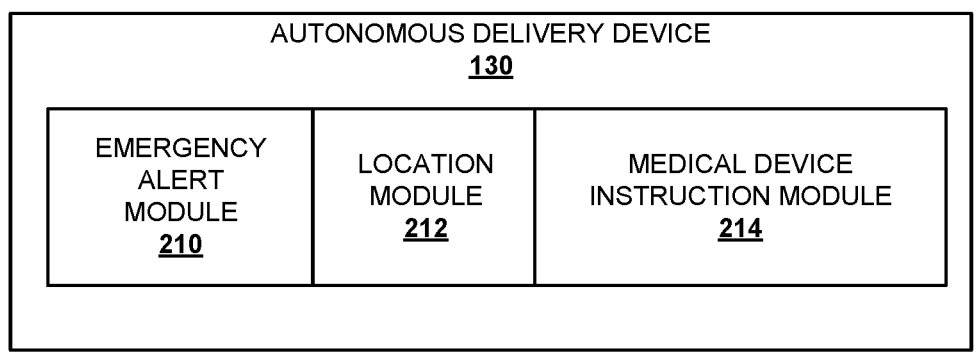
FIG. 2 is a schematic diagram illustrating an autonomous delivery device in accordance with an embodiment of the present disclosure.

FIG. 2 is a schematic diagram illustrating an autonomous delivery device 130 in accordance with an embodiment of the present disclosure. As stated above, the autonomous delivery device 130 can be any type of unmanned automated delivery device or machine such as, but not limited to, a drone, a robot, and an autonomous vehicle. In the depicted embodiment, the autonomous delivery device 130 includes an emergency alert module 210, a location module 212, and a medical device instruction module 214.

The emergency alert module 210 is configured to receive an alert notification and related information from the autonomous medical delivery system 100 about a medical alert. The related information can include an access or unlock code or other data (e.g., thumbprint, facial image) for unlocking or releasing the medical item from the autonomous delivery device 130 to prevent unauthorized access or use of the medical item.

The location module 212 is configured to receive a location of the medical alert. Based on the location, the location module 212 can determine the optimum route for traveling to the location of the medical alert. For example, if the autonomous delivery device 130 is a robot/machine that has wheels or is an autonomous delivery vehicle that is located within an amusement park, the location module 212 can be configured to retrieve a map containing routes within the amusement park for determining an optimum path. Similar determinations can be made for a flying autonomous delivery device 130. Alternatively, the location module 212 can include instructions for enabling an autonomous delivery device 130 to manually train itself on a particular area via photos, maps, or by physically traversing the area. For example, in an embodiment, the autonomous delivery device 130 can be configured to move about a location during off hours or during regular business hours to train itself on its surroundings using positional, sight and distance sensors. The location module 212 can map out the environment to more easily find routes to possible locations where the medical items might be needed, such as inside a building, mall, or an amusement park. The autonomous delivery device 130 can include sensors, cameras, and other collision avoidance systems to enable navigation and to avoid obstacles and people within its path. In some embodiments, the location module 212 can also employ artificial intelligence (AI) or machine learning to improve upon the placement of the autonomous delivery device 130 and/or medical items based on past locations of alerts, the types of alerts, frequency of occurrences, average number of injury per occurrence, etc. In some embodiments, another device or machine may be configured to perform the mapping feature and provide the mapping information to the location module 212 for use in instructing the autonomous delivery device 130. The mapping device or machine can be of another type than the delivery device. For example, the mapping device and the delivery device can use different propulsion technique. For instance, a mapping drone could be used to provide a map to a wheeled vehicle for enabling the wheeled vehicle to determine routing options.

The medical device instruction module 214 can be configured to select one or more medical items to deliver to the location of the medical alert. For example, if the medical alert indicates that a person is having a heart attack, but also suffered an open wound from falling, the medical device instruction module 214 can select an AED, medical gloves to protect against pathogens, the appropriate size/amount of bandages for the open wound, and other appropriate items (e.g., blankets if the weather is cold for outside injuries). The medical device instruction module 214 can also select the appropriate videos for assisting a registered user to use one or more of the medical items. For instance, a video may demonstrate how to properly bandage an open wound, use the AED, or perform the Heimlich maneuver if a person is choking. Alternatively, the medical device instruction module 214 can establish a live communication channel with medical personnel to assist the registered user. The live medical personnel can be displayed on a visual screen of the autonomous delivery device 130, and can utilize a microphone, camera, and speaker on the autonomous delivery device 130 to assist the trained user with the medical emergency.

In some embodiments, the medical device instruction module 214 can include instructions for communicating with other systems to allow removal of obstacles or faster delivery. For example, in some embodiments, the medical device instruction module 214 can include instructions for communicating with traffic lights, doors locks, elevators, security system, and home automation systems, etc.

Figure 3:
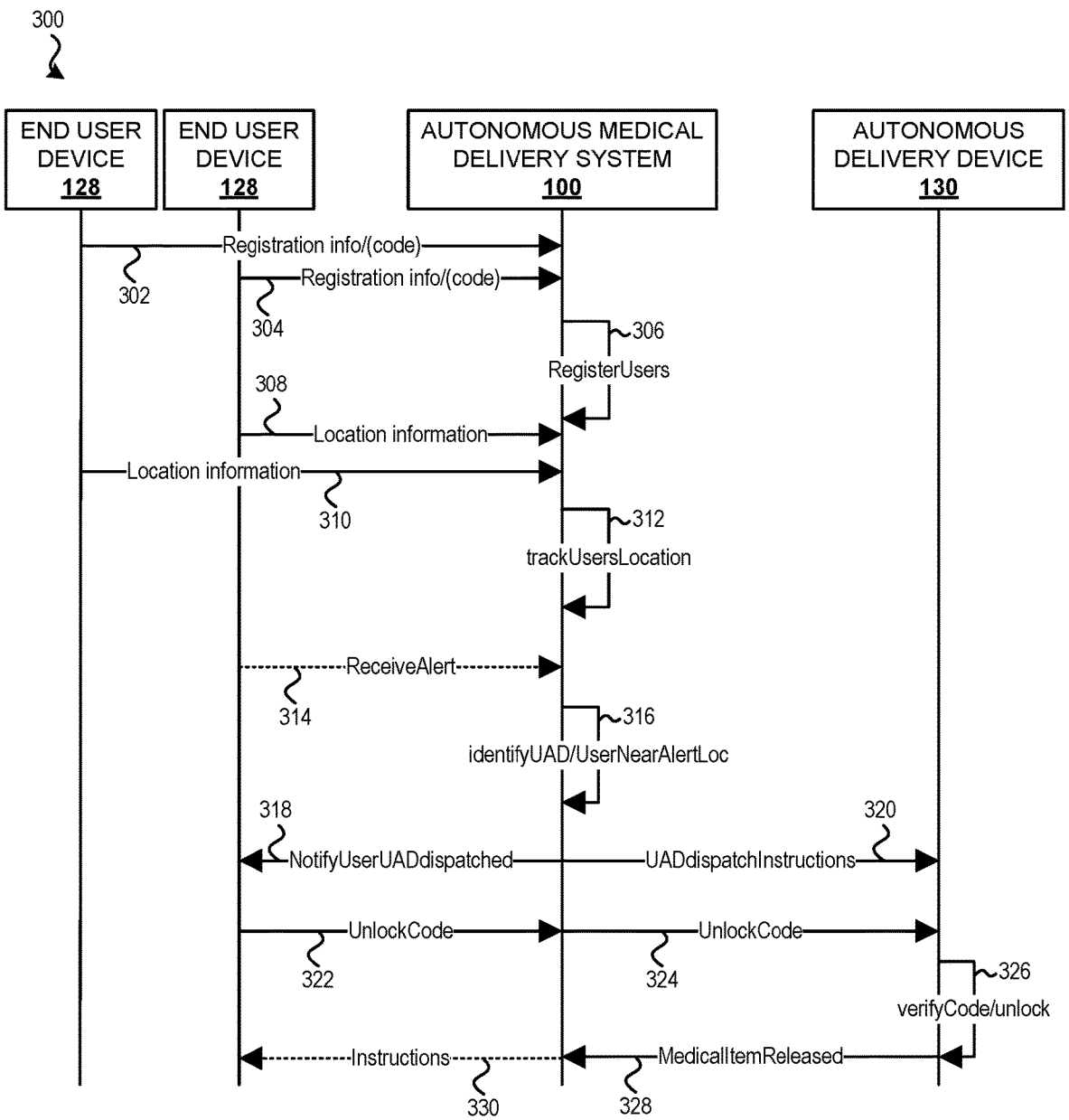
FIG. 3 is a sequence diagram illustrating a sequence of actions for providing a medical item in accordance with an embodiment of the present disclosure.

FIG. 3 is a sequence diagram 300 illustrating a sequence of actions between one or more end user devices 128, the autonomous medical delivery system 100, and an autonomous delivery device 130 for providing a medical item in accordance with an embodiment of the present disclosure. The sequence diagram 300 begins with the autonomous medical delivery system 100 receiving registration information from one or more of the end user devices 128 (steps 302, 304). Registration information can include various user information such as, but not restricted to, user name, device information, contact information, medical certifications, and a registration code indicating the user has completed training for a particular medical item/procedure. The registration information can also include location tracking authorization of the end user devices 128.

At step 306, the autonomous medical delivery system 100 registers the end user devices 128 after verifying the received information. As part of the process, the autonomous medical delivery system 100 may transmit a user registration verification notice to the end user devices 128. Once the end user devices 128 are registered with the autonomous medical delivery system 100, the end user devices 128 periodically (e.g., every few seconds) transmit their location information to the autonomous medical delivery system 100 (steps 308, 310). The autonomous medical delivery system 100 tracks and stores the location of the end user devices 128 at step 312. The autonomous medical delivery system 100 can store the locations of medical items and the distance of the end user devices 128 to the medical items to identify the nearest user/medical items in case of a medical emergency.

At step 314, the autonomous medical delivery system 100 receives an alert indicating a medical emergency. The alert can be received from various sources including, but are not limited to, an end user device 128, an emergency activation device 126, and an audio and/or video device 124. For example, a trained user of a medical item/device may witness a medical emergency and transmit an alert to the autonomous medical delivery system 100 using an end user device 128. In some embodiments, the alert may also be received from non-trained users that register with the autonomous medical delivery system 100, any user that has downloaded an application or using other means (e.g., through a website or texting/calling a certain number) that is capable of communicating with the autonomous medical delivery system 100, from an emergency service notification, or from a security company for enabling additional sources for alert notifications. In some embodiments, the alert may also be received from a monitoring device. For example, in an embodiment, a monitoring device, sensor device, home camera system, or home assistance device (e.g., Amazon® Echo® or Alexa® device, or Google® home device) may be used to monitor for an audio call for help or visual signs of distress. This may be especially useful in senior care facilities or for the elderly that live at home by themselves.

At step 316, the autonomous medical delivery system 100 identifies the nearest trained user based on the location information of the end user devices 128. In some cases, this may be the end user device 128 that transmitted the medical alert to the autonomous medical delivery system 100. At step 318, the autonomous medical delivery system 100 transmits a medical emergency notification containing information related to the medical alert to the nearest end user device 128. In some embodiments, the autonomous medical delivery system 100 may transmit the medical emergency notification to more than one end user device 128 within proximity of the medical emergency as a precautionary measure to provide backup in case a trained user does not respond to a medical emergency notification. Additionally, in some embodiments, the autonomous medical delivery system 100 may transmit the medical emergency notification to more than one end user device 128 if there are multiple injuries (e.g., a bus accident). The notification may indicate that multiple people are in need of assistance.

In an embodiment, the medical emergency notification can be transmitted and displayed using a specially configured application for communicating with the autonomous medical delivery system 100, through text messaging, via voice communications, using the wireless emergency alerts system, or through any other communication means. In some embodiments, if granted permission by a user, the alert notification may turn on a user's device that has been powered off or logged off, and turn on notifications or audio notifications if disabled.

The medical emergency notification can indicate that an autonomous delivery device 130 carrying a medical item is being dispatched to the location of the medical emergency. The medical emergency notification can also include an unlock or security code that will be used to access the medical items when delivered by an autonomous delivery devices 130.

The autonomous medical delivery system 100, at step 320, transmits instructions related to the medical alert to an autonomous delivery device 130 to dispatch a medical item to the location of the medical emergency. In some embodiments, if needed, multiple autonomous delivery devices 130 may be dispatched to the emergency location (e.g., if there are multiple traumas or different medical items are needed). The instructions can include location information of the medical emergency, flight or maneuver instructions, the type/number of medical items, authorize user unlock code or other forms of security, and other relevant information.

In an embodiment, once the autonomous delivery devices 130 arrives at the location of the medical emergency, the user, using the end user device 128, may transmit an unlock code to the autonomous medical delivery system 100, at step 322, which is verified and relayed to the autonomous delivery devices 130, at steps 324 and 326, to enable release or access to the medical items to only the authorized user. For example, the autonomous delivery devices 130 may contain a secure compartment that is only accessible when the correct unlock code is received. In some embodiments, the unlock code can be entered directly into the autonomous delivery devices 130 (e.g., via a touchscreen or keyboard on the autonomous delivery devices 130).

In an embodiment, at step 328, the autonomous delivery devices 130 can transmit a notification to the autonomous medical delivery system 100 once the medical item is released to the user. In certain embodiments, at step 330, the autonomous medical delivery system 100 can transmit instructions for using the medical item to the end user device 128, these instructions can assist the user in recalling his training and proper use of the medical item. In some embodiments, instructions may be presented to the user via a display screen on the autonomous delivery devices 130. Still, in some embodiments, a live communication session may be established, either via the end user device 128 or autonomous delivery devices 130, with a medical provider to assist the user with the medical emergency. In certain embodiments, vitals or other information (e.g., respiration, blood pressure, and/or heart information) may be relayed or transmitted to a remote system such as a doctor or hospital system for remote monitoring.

Figure 4:
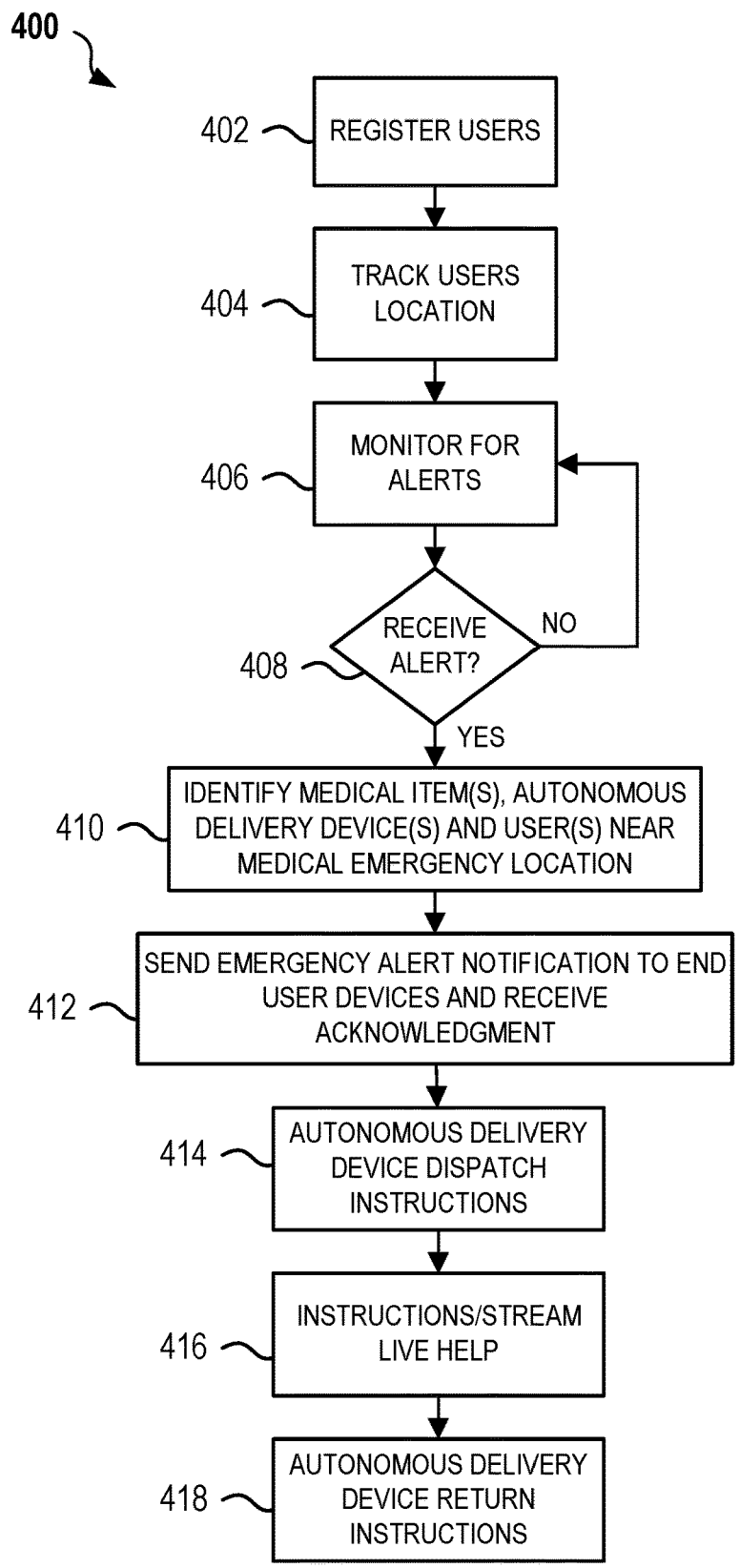
FIG. 4 is flowchart illustrating a process performed by an autonomous medical delivery system for providing a medical item in accordance with an embodiment of the present disclosure.

FIG. 4 is a flowchart illustrating a process 400 performed by an autonomous medical delivery system for providing a medical item in accordance with an embodiment of the present disclosure. For example, in one embodiment, the process 400 can be performed by the autonomous medical delivery system 100 of FIG. 1. In the depicted embodiment, the process 400 begins at step 402 by registering users/user devices. In some embodiments, if a user has been trained on the proper use of a medical item (e.g., through a certification class), the user is provided with a registration code that can be used in the registration process to indicate that the user is trained/certified in the use of a particular medical item.

Once the user/user devices are registered, the process 400, at step 404, tracks the location of the end user devices. The process 400, at step 406, monitors for medical alerts indicating a medical emergency. The medical alerts can be received from various sources as described above. If a medical alert is received at step 408, the process 400, at step 410, identifies an autonomous delivery device and a user device located near the location of the medical emergency. At step 412, the process 400 can send an emergency alert notification to the end user device(s) to alert the users of the medical emergency. In an embodiment, the emergency alert notification can include an estimated time for a medical item to be delivered and/or an estimated time for the registered personnel to reach the location of the incident. The alert can also provide a best route or travel instructions to the user to minimize any delay in reaching the location of the incident (e.g., take subway A at station B, exit station D, and go north 1 block). In some embodiments, the process 400 can receive a confirmation or acknowledgment message from the end user device(s) to indicate that they are responding to the medical emergency. In some embodiments, the alert can also include instructions for moving an injured person, if safe to do so, to an area more accessible to autonomous delivery device to enable faster delivery of the medical item. In some embodiments, the alert can also instruct the trained user that the medical item will be delivered to a location other than the location of the person in need. For example, if the autonomous delivery device is a robot or vehicle with wheels that cannot access tight corridors or stairways, the alert may instruct the user to pick up the medical item at a particular entrance of a building or at some other nearby designated location.

At step 414, the process 400 transmits instructions to the identified autonomous delivery device(s) located near the location of the medical emergency to dispatch delivery of one or more medical items to the location of the medical emergency via the autonomous delivery device(s). As described above, in some embodiments, the process 400 can receive an unlock or security code to verify that only trained users are able to access the medical items from the autonomous delivery device.

At step 416, the process 400 can transmit instructions or establish a live communication session with a medical personnel to assist the trained user with the medical emergency. In various embodiments, the instructions can be played or the communication session can be established using the end user device or the autonomous delivery device. Once the medical emergency has been handled, the process 400, at step 418, can initiate instructions for the autonomous delivery device(s) to return to a particular location, with the process 400 terminating thereafter.

Figure 5:
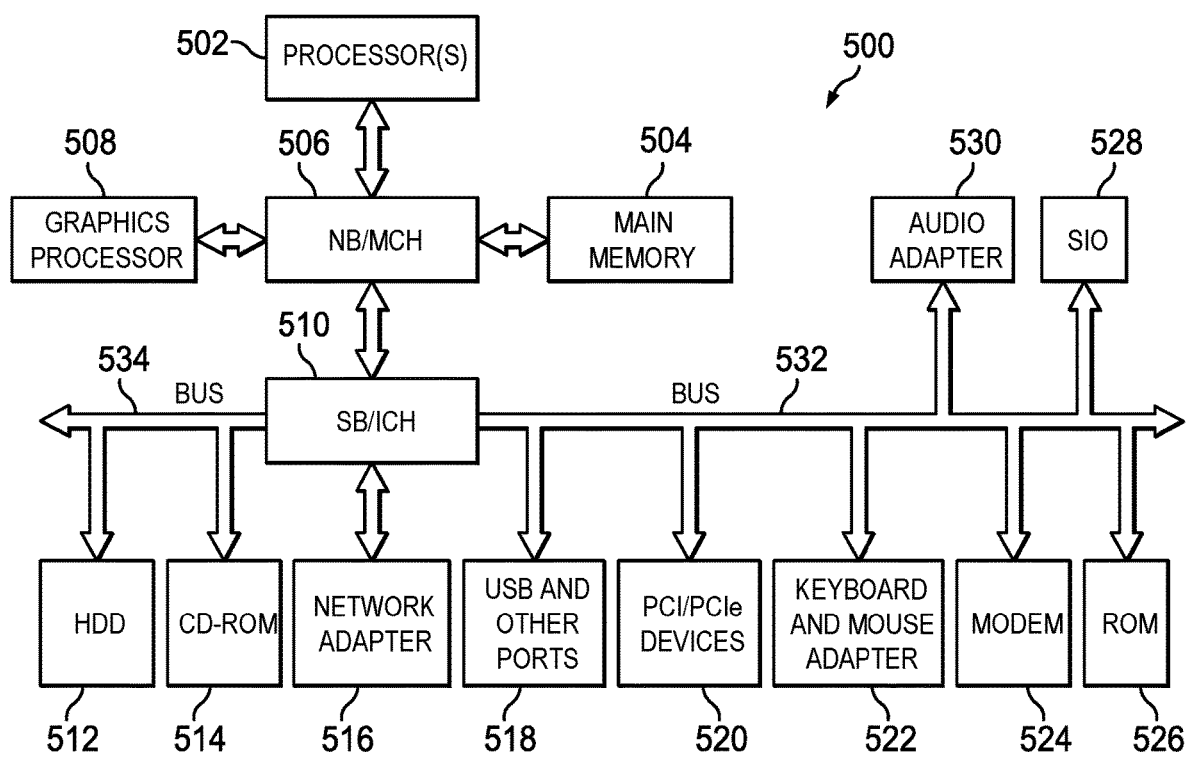
FIG. 5 is a block diagram illustrating a hardware architecture of a data processing system according to an embodiment of the present disclosure.

FIG. 5 is a block diagram illustrating a hardware architecture of a data processing system 500 according to an embodiment of the present disclosure in which aspects of the illustrative embodiments may be implemented. For example, in one embodiment, the autonomous medical delivery system 100 of FIG. 1 may be implemented using the data processing system 500. Additionally, the data processing system 500 may be configured to store and execute instructions for performing the process described in FIGS. 3 and 4. In the depicted example, the data processing system 500 employs a hub architecture including north bridge and memory controller hub (NB/MCH) 506 and south bridge and input/output (I/O) controller hub (SB/ICH) 510. Processor(s) 502, main memory 504, and graphics processor 508 are connected to NB/MCH 506. Graphics processor 508 may be connected to NB/MCH 506 through an accelerated graphics port (AGP). A computer bus, such as bus 532 or bus 534, may be implemented using any type of communication fabric or architecture that provides for a transfer of data between different components or devices attached to the fabric or architecture.

In the depicted example, network adapter 516 connects to SB/ICH 510. Audio adapter 530, keyboard and mouse adapter 522, modem 524, read-only memory (ROM) 526, hard disk drive (HDD) 512, compact disk read-only memory (CD-ROM) drive 514, universal serial bus (USB) ports and other communication ports 518, and peripheral component interconnect/peripheral component interconnect express (PCI/PCIe) devices 520 connect to SB/ICH 510 through bus 532 and bus 534. PCI/PCIe devices may include, for example, Ethernet adapters, add-in cards, and personal computing (PC) cards for notebook computers. PCI uses a card bus controller, while PCIe does not. ROM 526 may be, for example, a flash basic input/output system (BIOS). Modem 524 or network adapter 516 may be used to transmit and receive data over a network.

HDD 512 and CD-ROM drive 514 connect to SB/ICH 510 through bus 534. HDD 512 and CD-ROM drive 514 may use, for example, an integrated drive electronics (IDE) or serial advanced technology attachment (SATA) interface. In some embodiments, HDD 512 may be replaced by other forms of data storage devices including, but not limited to, solid-state drives (SSDs). A super I/O (SIO) device 528 may be connected to SB/ICH 510. SIO device 528 may be a chip on the motherboard that is configured to assist in performing less demanding controller functions for the SB/ICH 510 such as controlling a printer port, controlling a fan, and/or controlling the small light emitting diodes (LEDS) of the data processing system 500.

The data processing system 500 may include a single processor 502 or may include a plurality of processors 502.

Additionally, processor(s) 502 may have multiple cores. For example, in one embodiment, data processing system 500 may employ a large number of processors 502 that include hundreds or thousands of processor cores. In some embodiments, the processors 502 may be configured to perform a set of coordinated computations in parallel.

An operating system is executed on the data processing system 500 using the processor(s) 502. The operating system coordinates and provides control of various components within the data processing system 500 in FIG. 5. Various applications and services may run in conjunction with the operating system. Instructions for the operating system, applications, and other data are located on storage devices, such as one or more HDD 512, and may be loaded into main memory 504 for execution by processor(s) 502. In some embodiments, additional instructions or data may be stored on one or more external devices. The processes described herein for the illustrative embodiments may be performed by processor(s) 502 using computer usable program code, which may be located in a memory such as, for example, main memory 504, ROM 526, or in one or more peripheral devices.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random-access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented method, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. As an example, the autonomous medical delivery system 100 depicted in FIG. 1 is just one embodiment and is not intended to limit the scope of the claims. For instance, in other embodiments, the autonomous medical delivery system 100 can include other modules not specifically described herein, or can combine or eliminate one or more of the various depicted modules. Further, the steps of the methods described herein may be carried out in any suitable order, or simultaneously where appropriate. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for automated delivery of a medical item, the computer-implemented method comprising:
receiving registration information from a plurality of trained users, the registration information including a registration code indicating which medical item that a user is trained to use, the registration information received from a computer-based registration application submitted by the plurality of trained users pursuant to a registration process;
verifying the registration code is valid prior to registering a trained user;
tracking locations of the trained users via end user devices of the trained users;
receiving at least one of audio and video data;
analyzing the at least one audio and video data to identify phrases, movements, positions, or actions indicative of a medical emergency;
identifying a medical item that would assist in the medical emergency;
determining a location of the medical emergency;
identifying a trained user near the location of the medical emergency that is trained to use the medical item based on whether the registration information of the trained user includes the registration code corresponding to the medical item;
dispatching an autonomous delivery device to deliver the medical item to the location of the medical emergency; and
alerting the trained user that the medical item is being dispatched to the location of the medical emergency.

2. The computer-implemented method of claim 1, further comprising transmitting an unlock authorization code to the end user device of the trained user, the unlock authorization code enabling access to the medical item from a secure compartment of the autonomous delivery device.

3. The computer-implemented method of claim 1, further comprising using the registration code to identify the trained user that is trained to use the medical item.

4. The computer-implemented method of claim 1, further comprising receiving the registration information from a mobile application on the end user devices of the trained users.

5. The computer-implemented method of claim 4, further comprising receiving the at least one of audio and video data from the mobile application on the end user devices of the trained user.

6. The computer-implemented method of claim 1, further comprising establishing a live communication session with medically trained personnel via a communication device of the autonomous delivery device.

7. The computer-implemented method of claim 1, wherein the at least one of audio and video data is received from a home assistance device at the location of the medical emergency.

8. The computer-implemented method of claim 1, wherein the at least one of audio and video data is received from an emergency activation device.

9. A system configured to automate delivery of a medical item, the system comprising memory for storing instructions, and a processor configured to execute the instructions to:
receive registration information for a plurality of trained users, the registration information including a registration code indicating which medical item that a user is trained to use, the registration information received from a computer-based registration application submitted by the plurality of trained users pursuant to a registration process;
verify that the registration code is valid;
register the user as a trained user in response to validating the registration code;
track locations of the trained users via an end user device of the trained users;
receive at least one of audio and video data;
analyze the at least one audio and video data to identify phrases, movements, positions, or actions indicative of a medical emergency;
identify a medical item that would assist in the medical emergency;
determine a location of the medical emergency;
identify a trained user that is trained to use the medical item near the location of the medical emergency based on whether the registration information of the trained user includes the registration code corresponding to the medical item;
dispatch an autonomous delivery device to deliver the medical item to the location of the medical emergency; and
alert the trained user that the medical item is being dispatched to the location of the medical emergency.

10. The system of claim 9, wherein the processor is configured to further execute the instructions to transmit an unlock authorization code to the end user device of the trained user, the unlock authorization code enabling access to the medical item from a secure compartment of the autonomous delivery device.

11. The system of claim 9, wherein the processor is configured to further execute the instructions to provide prerecorded instructions for using the medical item.

12. The system of claim 9, wherein the processor is configured to further execute the instructions to establish a live communication session with medically trained personnel through the end user device.

13. The system of claim 9, wherein the processor is configured to further execute the instructions to establish a live communication session with medically trained personnel via a communication device of the autonomous delivery device.

14. The system of claim 9, wherein the at least one of audio and video data is received from the end user device of the trained user.

15. The system of claim 9, wherein the at least one of audio and video data is received from a home assistance device at the location of the medical emergency.

16. The system of claim 9, wherein the at least one of audio and video data is received from an emergency activation device.

17. A computer program product for providing automated delivery of a medical item, the computer program product comprising a computer readable storage medium having program instructions embodied therewith, the program instructions executable by a processor to cause the processor to:
receive registration information for a plurality of trained users, the registration information including a registration code indicating which medical item that a user is trained in a use, the registration information received from a computer-based registration application submitted by the plurality of trained users pursuant to a registration process;
verify that the registration code is valid;
register the user as a trained user in response to validating the registration code;
track locations of the trained users via an end user device of the trained users;
receive at least one of audio and video data;
analyze the at least one audio and video data to identify phrases, movements, positions, or actions indicative of a medical emergency;
identify a medical item that would assist in the medical emergency;
determine a location of the medical emergency;
identify a trained user that is trained to use the medical item near the location of the medical emergency based on whether the registration information of the trained user includes the registration code corresponding to the medical item;
dispatch an autonomous delivery device to deliver the medical item to the location of the medical emergency; and
alert the trained user that the medical item is being dispatched to the location of the medical emergency.

18. The computer program product of claim 17, wherein the program instructions executable by the processor comprises instructions to transmit an unlock authorization code to the end user device of the trained user, the unlock authorization code enabling access to the medical item from a secure compartment of the autonomous delivery device.

19. The computer program product of claim 17, wherein the program instructions executable by the processor comprises instructions to establish a live communication session with medically trained personnel through the end user device of the trained user.

20. The computer program product of claim 17, wherein the program instructions executable by the processor comprises instructions to receive the at least one of audio and video data from an emergency activation device.

\* \* \* \* \*